US011844654B2

(12) United States Patent
Cadieu et al.

(10) Patent No.: US 11,844,654 B2
(45) Date of Patent: Dec. 19, 2023

(54) MID-PROCEDURE VIEW CHANGE FOR ULTRASOUND DIAGNOSTICS

(71) Applicant: Caption Health, Inc., Brisbane, CA (US)

(72) Inventors: Charles Cadieu, Menlo Park, CA (US); Michael G. Cannon, Haverford, PA (US); Ali Chaudhry, San Francisco, CA (US); Ha Hong, San Ramon, CA (US); Kilian Koepsell, San Francisco, CA (US); Nripesh Parajuli, Millbrae, CA (US); Nicolas Poilvert, Seattle, WA (US)

(73) Assignee: Caption Health, Inc., Brisbane, CA (US)

( * ) Notice: Subject to any disclaimer, the term of this patent is extended or adjusted under 35 U.S.C. 154(b) by 68 days.

(21) Appl. No.: 16/544,582

(22) Filed: Aug. 19, 2019

(65) Prior Publication Data

US 2021/0052253 A1    Feb. 25, 2021

(51) Int. Cl.
*A61B 8/00* (2006.01)
*A61B 8/08* (2006.01)
(Continued)

(52) U.S. Cl.
CPC .............. *A61B 8/5223* (2013.01); *A61B 8/08* (2013.01); *A61B 8/463* (2013.01); *G06T 7/0012* (2013.01);
(Continued)

(58) Field of Classification Search
CPC ......... A61B 8/5223; A61B 8/08; A61B 8/463; G06T 7/0012
See application file for complete search history.

(56) References Cited

U.S. PATENT DOCUMENTS 6,314,165 B1    11/2001    Junqua et al.
6,315,724 B1    11/2001    Berman et al.
(Continued)

FOREIGN PATENT DOCUMENTS

CA    2950868 A1    6/2018
EP    2807978 A1    12/2014
(Continued)

OTHER PUBLICATIONS

Nov. 10, 2021 Non-Final Office Action U.S. Appl. No. 15/831,375.
(Continued)

*Primary Examiner* — Joel Lamprecht

(57) ABSTRACT

An ultrasound guidance dynamic progression method includes selecting a predetermined ultrasound diagnostic workflow in memory of an ultrasound diagnostic computing system, the workflow including a sequence of views of a target organ. The method further includes selecting a first view in the sequence and presenting guidance in a display of the computing system for the first view, for instance visual, audible or haptic feedback. The method yet further includes acquiring imagery in the computing system in association with the first view, and detecting an anomalous feature of the acquired imagery. Finally, the method includes selecting a different view in the sequence as a substitute for a next one of the views in the sequence in response to having detected the anomalous feature, and further presenting different guidance in the display for the different view in lieu of guidance for the next one of the views.

9 Claims, 2 Drawing Sheets

(51) Int. Cl.
  *G06T 7/00* (2017.01)
  *A61B 5/055* (2006.01)
  *A61B 8/06* (2006.01)

(52) U.S. Cl.
  CPC .............. *A61B 5/055* (2013.01); *A61B 8/06* (2013.01); *A61B 8/483* (2013.01); *A61B 8/5207* (2013.01)

(56) References Cited

U.S. PATENT DOCUMENTS

| | | | |
|---|---|---|---|
| 10,426,442 B1 * | 10/2019 | Schnorr | A61B 8/085 |
| 10,993,697 B2 * | 5/2021 | Nouri | G06T 11/60 |
| 2003/0192557 A1 | 10/2003 | Krag et al. | |
| 2004/0019270 A1 | 1/2004 | Takeuchi | |
| 2012/0035868 A1 | 2/2012 | Roche et al. | |
| 2012/0207359 A1 | 8/2012 | Konukoglu et al. | |
| 2014/0221832 A1 | 8/2014 | El-Zehiry et al. | |
| 2016/0113632 A1 | 4/2016 | Ribes et al. | |
| 2016/0174934 A1 | 6/2016 | Cong et al. | |
| 2016/0374644 A1 | 12/2016 | Mauldin, Jr. et al. | |
| 2017/0105701 A1 | 4/2017 | Pelissier et al. | |
| 2017/0143427 A1 | 5/2017 | Grady et al. | |
| 2017/0181726 A1 | 6/2017 | Schneider et al. | |
| 2017/0215842 A1 | 8/2017 | Ryu et al. | |
| 2017/0262982 A1 | 9/2017 | Pagoulatos et al. | |
| 2017/0265846 A1 | 9/2017 | Sui et al. | |
| 2017/0273669 A1 | 9/2017 | Schneider | |
| 2017/0360401 A1 | 12/2017 | Rothberg et al. | |
| 2017/0360411 A1 | 12/2017 | Rothberg et al. | |
| 2018/0153505 A1 | 6/2018 | Cadieu et al. | |
| 2018/0344286 A1 | 12/2018 | Mienkina et al. | |
| 2019/0015076 A1 | 1/2019 | Rouet et al. | |
| 2019/0125301 A1 | 5/2019 | Jago et al. | |
| 2019/0142388 A1 | 5/2019 | Gonyeau et al. | |
| 2019/0148011 A1 | 5/2019 | Rao et al. | |
| 2020/0043129 A1 | 2/2020 | Radulescu et al. | |
| 2020/0245968 A1 | 8/2020 | Nellur Prakash et al. | |
| 2020/0245970 A1 | 8/2020 | Cadieu et al. | |
| 2020/0359991 A1 | 11/2020 | Xu et al. | |

FOREIGN PATENT DOCUMENTS

| | | | |
|---|---|---|---|
| EP | 3530190 | 8/2019 | |
| WO | WO-2015150932 A1 | 10/2015 | |
| WO | WO-2019201726 A1 * | 10/2019 | ............. G16H 50/30 |

OTHER PUBLICATIONS

Dec. 27, 2021 Non-Final Office Action U.S. Appl. No. 16/264,310.
Feb. 20, 2020 Non-Final Office Action U.S. Appl. No. 15/831,375.
Apr. 1, 2021 Final Office Action U.S. Appl. No. 15/831,375.
May 18, 2022 Non-Final Office Action U.S. Appl. No. 15/831,375.
Jun. 22, 2020 Final Office Action U.S. Appl. No. 15/831,375.

* cited by examiner

MID-PROCEDURE VIEW CHANGE FOR ULTRASOUND DIAGNOSTICS

BACKGROUND OF THE INVENTION

Field of the Invention

The present invention relates to ultrasound imaging and more particularly to ultrasound image acquisition.

Description of the Related Art

Medical imaging refers to the process of creating a visual representation of an interior portion of a mammalian body for the purpose of clinical analysis and medical intervention. Medical imaging seeks to reveal internal structures hidden by the exterior of the body so as to facilitate the diagnosis and treatment of disease. Medical imaging incorporates several different image acquisition methodologies and corresponding radiological devices technologies. Common techniques include X-ray radiography including computerized tomography (CT), magnetic resonance imaging (MRI), medical ultrasonography or ultrasound, endoscopy, elastography, tactile imaging, thermography, medical photography and nuclear medicine functional imaging techniques as positron emission tomography (PET) and Single-photon emission computed tomography (SPECT). Depending upon the desired use of the imagery for the purpose of a medical diagnosis or the targeting of specific tissue or a particular organ or portion of an organ, different techniques and devices for different imagery may be preferred.

Ultrasound imaging, also known as sonography, is a medical imaging technique that employs high-frequency sound waves to view three-dimensional structures inside the body of a living being. Because ultrasound images are captured in real-time, ultrasound images also show movement of the internal organs of the body as well as blood flowing through the blood vessels of the human body and the stiffness of tissue. Unlike x-ray imaging, ultrasound imaging does not involve ionizing radiation thereby allowing prolonged usage of ultrasound imaging without threatening tissue and internal organ damage from prolonged radiation exposure.

To acquire ultrasound imagery, during an ultrasound exam, a transducer, commonly referred to as a probe, is placed directly on the skin or inside a body opening. The probe is coupled to image generation circuitry that includes circuitry adapted to transmit and receive signals to and from the probe, and may include a beamformer, though synthetic aperture imaging systems may use retrospective image formation reducing the need for beamforming and scan conversion functions. A thin layer of gel is applied to the skin so that the ultrasound waves are transmitted from the probe through the medium of the gel into the body. The ultrasound image is produced based upon a measurement of the reflection of the ultrasound waves off the body structures. The strength of the ultrasound signal, measured as the amplitude of the detected sound wave reflection, and the time taken for the sound wave to travel through the body provide the information necessary to compute an image of target structures of the body. As well, the "Doppler" effect may be used in ultrasound imagery to measure the velocity and direction of fluid flow within the structures of the body (namely, blood).

Compared to other prominent methods of medical imaging, ultrasound presents several advantages to the diagnostician and patient. First and foremost, ultrasound imaging provides images in real-time. As well, ultrasound imaging requires equipment that is portable and can be brought to the bedside of the patient. Further, as a practical matter, the ultrasound imaging equipment is substantially lower in cost than other medical imaging equipment, and as noted, does not use harmful ionizing radiation. Even still, ultrasound imagery is not without challenge.

For example, in some instances, an attempted view of a target organ may be incomplete omitting key features of the target organ from the view due to anatomical limitations or an improper placement of the imaging sensor. In this regard, as to the term "view", the ultrasound imaging of a target area of the body may be achieved from many different "views" utilizing the ultrasound probe. Each view may be achieved through a combination of position and pose of the probe such that the angle and approach of the ultrasound probe generally results in a different perspective "view" of the target area. Generally, a particular view of the target area presented in an ultrasound image may be preferred depending upon the desired use of the imagery for the purpose of a medical diagnosis or the targeting of specific tissue or a particular organ or portion thereof. More to the point, different views of the same target area produce imagery with emphasis on different anatomical features such that some views are known to have the highest probability of producing imagery of a feature of interest. As well, different views can also be required in order to perform measurements that are used for diagnostic purposes.

Thus, depending upon the particular feature of interest, the operator must first know the desired view to best image the feature of interest and then, with respect to the portion of the body selected for imaging and the desired view, the skilled operator must know where to initially place the ultrasound probe on the body. Then, the skilled operator must know how to spatially orient the probe and finally, the skilled operator must know where to move the probe so as to acquire the desired imagery, including acquiring additional views. Generally, the ultrasound operator is guided in the initial placement, orientation and movement of the probe based upon the visual feedback provided by the imagery produced during the ultrasound. As it will be recognized, then, essentially, the navigation of the probe is a manual process consisting of iterative trial and error and requires specialized knowledge and expertise on the part of the ultrasound operator—especially in the selection of a route of views through which the probe must move in order to produce a complete exam.

Importantly, given the nature of conventional ultrasound imaging, the resultant images of a target area of the body may vary in quality. That is to say, depending upon the operator, the clarity and focal point of a medical image may vary. As well, external factors such as the anatomical features of the body may inhibit clarity of key features of the target organ despite proper placement of the imaging sensor. Yet, whereas certain anatomical features may inhibit a quality image of a target area in one view, a different view of the same target area or even a slightly different target area may provide higher quality imagery of the anatomical feature sought for imaging by the practitioner. Thus, the operator must know through experience to shift efforts from acquiring imagery of the target area through one view to another view when the quality of imagery through the first view is substandard or when a particular structure of the target area is only partially viewable within the first view but desirable in light of the determination from the first view that an abnormality or anomalous condition justifies clearer visualization of the particular structure through a presentation of a different view than the first view more likely to produce the clearer visualization. As can be seen, then, the production of quality ultrasound images remains highly dependent upon a skilled operator.

BRIEF SUMMARY OF THE INVENTION

Embodiments of the present invention address deficiencies of the art in respect to ultrasound imaging and provide a novel and non-obvious method, system and computer program product for route diversion during ultrasound diagnostics. In an embodiment of the invention, an ultrasound guidance dynamic progression method includes selecting a predetermined ultrasound diagnostic workflow in memory of an ultrasound diagnostic computing system, the workflow including a sequence of views of a target organ. The method further includes selecting a first one of the views in the sequence and presenting guidance, such as visual guidance, in a display of the computing system for the selected first one of the views. The method yet further includes acquiring imagery in the computing system in association with the selected first one of the views in the sequence, and detecting an anomalous feature of the target organ. Finally, the method includes selecting a different one of the views in the sequence as a substitute for a next one of the views responsive to the detection and further presenting different guidance in the display for the different one of the views in lieu of guidance for the next one of the views.

In one aspect of the embodiment, the method additionally includes identifying a measurement to be performed based on the detection of an anomalous feature of the target organ. In response, a different one of the views in the sequence is identified in association with the identified measurement. The different one of the views is then presented as a substitute for a next one of the views in order to perform the identified measurement. An exemplary measurement includes a measurement of fluid velocity—namely blood velocity in proximity to the target organ.

In another aspect of the embodiment, the anomalous feature is a presence of a visible feature in the acquired imagery. Conversely, in yet another aspect of the embodiment, the anomalous feature is an absence of a visible feature in the acquired imagery. In even yet another aspect of the embodiment, the visible feature is correlated in memory of the computing system with a disease. As well, in even yet another aspect of the embodiment, the visible feature is an irregular characteristic of a structure of the target organ. Finally, in even yet another aspect of the embodiment, the visible feature is extraneous material on a structure of the target organ.

In another embodiment of the invention, a data processing system is configured for ultrasound guidance dynamic progression. The system includes a computer with memory and at least one processor, a display coupled to the computer, image generation circuitry coupled to the computer and the display and an ultrasound imaging probe comprising a transducer connected to the image generation circuitry. The system also includes an ultrasound guidance dynamic progression module executing in the memory of the computer. The module includes program code enabled upon execution by the processor of the computer to select a predetermined ultrasound diagnostic workflow in memory of the computer, to select a first one of the views in the sequence and to present visual guidance in a display of the computer for the selected first one of the views. The program instructions further are enabled to acquire imagery in the computer in association with the selected first one of the views in the sequence, to detect an anomalous feature of the target organ and to select a different one of the views in the sequence as a substitute for a next one of the views responsive to the detection and further presenting different visual guidance in the display for the different one of the views in lieu of visual guidance for the next one of the views.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for ultrasound guidance dynamic progression. In accordance with an embodiment of the invention, a workflow is defined within an ultrasound diagnostic computing system for the ultrasound imaging of a target area of a body. In this regard, the workflow is defined to include multiple different views of the target area to be performed in a particular sequence. Then, upon commencing ultrasound imaging of the target area according to the workflow, guidance for a first one of the views is presented in a display of the ultrasound diagnostic computing system, and ultrasound imagery is acquired in association with the selected first view of the sequence.

In response to the acquired imagery, an association between the acquired imagery and a visible feature of the target area is detected, for instance the presence of a particular feature not expected to be visible within the imagery, or in the alternative, the absence of a particular feature expected to be visible within the imagery. Consequently, a different one of the views in the sequence is selected as a substitute for a next one of the views and different guidance is then presented in the display for the different one of the views in lieu of guidance for the next one of the views. In this way, the operator of the ultrasound diagnostic computing system deviates from the original planned sequence of the workflow mid procedure to provoke the acquisition of a more optimal view of the target area in consequence of the detected association.

Figure 1:
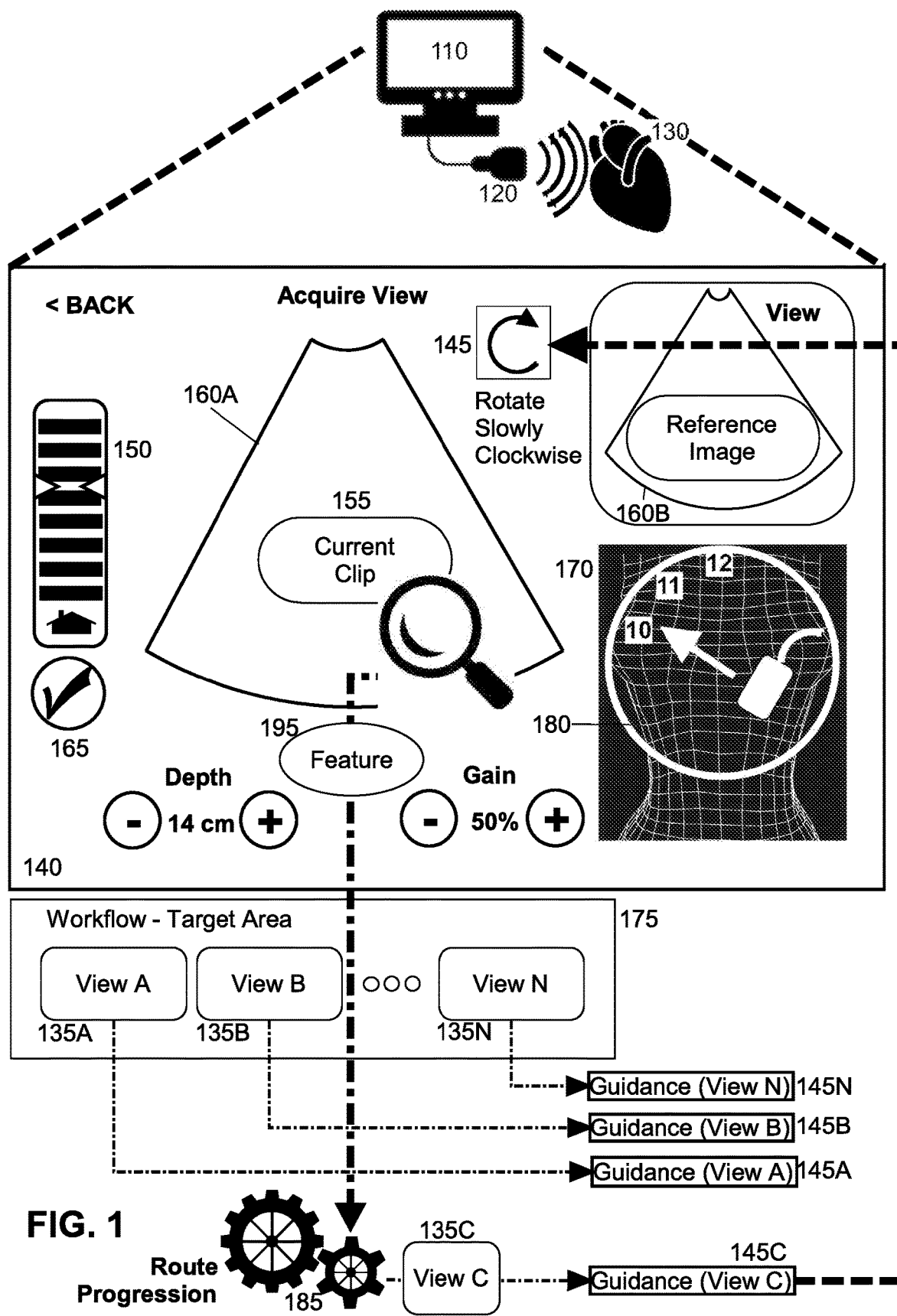
FIG. 1 is pictorial illustration of a process for ultrasound guidance dynamic progression.

FIG. 1 is pictorial illustration of a process for ultrasound guidance dynamic progression. As shown in FIG. 1, an ultrasound imaging system 110 with ultrasound imaging probe 120 conducts an ultrasound imaging operation in order to acquire a video clip as near real-time imagery 155 of a target organ 130. In conducting the ultrasound imaging operation, a workflow 175 of the target organ 130 is selected that includes a sequence of views 135A, 135B, 135N. For example, in connection with the imaging of a heart, the views 135A, 135B, 135N may include a parasternal long axis view, a parasternal short axis view, an apical two, three, four or five chamber view or a subcoastal view, to name a few examples.

For each of the views 135A, 135B, 135N, corresponding guidance 145A, 145B, 145N is determined and presented in sequence of the views 135A, 135B, 135N of the workflow 175 within the user interface 140 as respective graphical instructions 145. In this regard, the corresponding guidance 145A, 145B, 145N includes different directives for positioning and posing the ultrasound imaging probe 120 so as to produce the imagery 155 for a corresponding one of the views 135A, 135B, 135N. Exemplary guidance includes include, by way of example, the rotation of the ultrasound imaging probe 120 either in a clockwise or counter-clockwise direction, the movement of the ultrasound imaging probe 120 laterally away from the sternum, or medially towards the sternum, and the aiming of the imaging beam downwards or upwards by tilting the tail of the ultrasound imaging probe 120 upwards or downwards, respectively, slide downward, rock towards the indicator, rock away from the indicator, tilting the tail medially, or tilting the tail laterally, to name only a few examples.

To that end, a user interface 140 to the ultrasound imaging system 110 presents a contemporaneous display 160A of the imagery 155 acquired by the ultrasound imaging probe 120 of the target organ 130. A quality meter 150 is disposed in the user interface 140 and indicates a sliding scale of quality of the imagery 155 in the contemporaneous display 160A relative to a known view sought to be acquired for the target organ 130. To the extent that the imagery 155 is determined to have a corresponding quality value that meets or exceeds a threshold quality for the specified view, a success icon 165 is displayed in connection with the quality meter 150. As well, a previously acquired, ideal, reference image 160B of the target organ 130 according to the known view is displayed in the user interface 140.

Optionally, an additional portion 170 of the user interface 140 may be provided displaying an iconic image of a portion of a body in which the target organ 130 resides and a recommended movement of the ultrasound imaging probe 120 relative to the iconic image in order to achieve the specified view for the target organ 130. The additional portion of the user interface 170 includes a spatial orientation indicator 180 superimposed upon the iconic image of the portion of the body in which the target organ 130 resides. arranged as a clock angle indicator with twelve angularly equidistant positions. In this regard, only a relevant number of the clock angle positions are shown, as can be seen in FIG. 1, which positions are selected as a range towards which the ultrasound imaging probe 120 is known to move in order to acquire imagery of the specified view for the target organ 130. In this way, the combination of the recommended movement and the spatial orientation indicator 180 provide quick visual guidance to the operator of the ultrasound imaging system 110 in order to achieve a real-time image of sufficient quality for the selected view.

Of note, route progression logic 185 monitors the imagery 155 for each of the views 135A, 135B, 135N. In monitoring each imagery 155 for each of the views 135A, 135B, 135N, the route progression logic 185 may detect an anomalous feature 195. In this regard, the anomalous feature 195 can include imagery of structure not expected to be visible within the imagery 155. As well, the anomalous feature can include features related to the movement of fluids within the structure or through the structure or around the structure, for example, blood flow. Examples of the anomalous feature 195 include an irregular characteristic of a structure of the target organ 130, or extraneous material on a structure of the target organ 130. Either may be indicative of disease of the target organ 130. Alternatively, the anomalous feature 195 can include an absence of structure visible in the imagery 155, the absence of the structure also indicating disease of the target organ 130.

The route progression logic 185, upon detecting the anomalous feature 195, correlates the detected anomalous feature 195 with a different view 135C previously determined to provide for optimal imaging of the indicated disease, the different view 135C differing from the views 135A, 135B, 135N of the workflow 175. Consequently, guidance 145C for the different view 135C is presented as the respective graphical instruction 145 in the user interface 140 in lieu of the guidance 145A, 145B, 145N correlating to the next one of the views 135A, 135B, 135N of the workflow 175. In this way, the workflow 175 of views 135A, 135B, 135N can change dynamically mid-procedure responsive to the detection of the anomalous feature 195.

Figure 2:
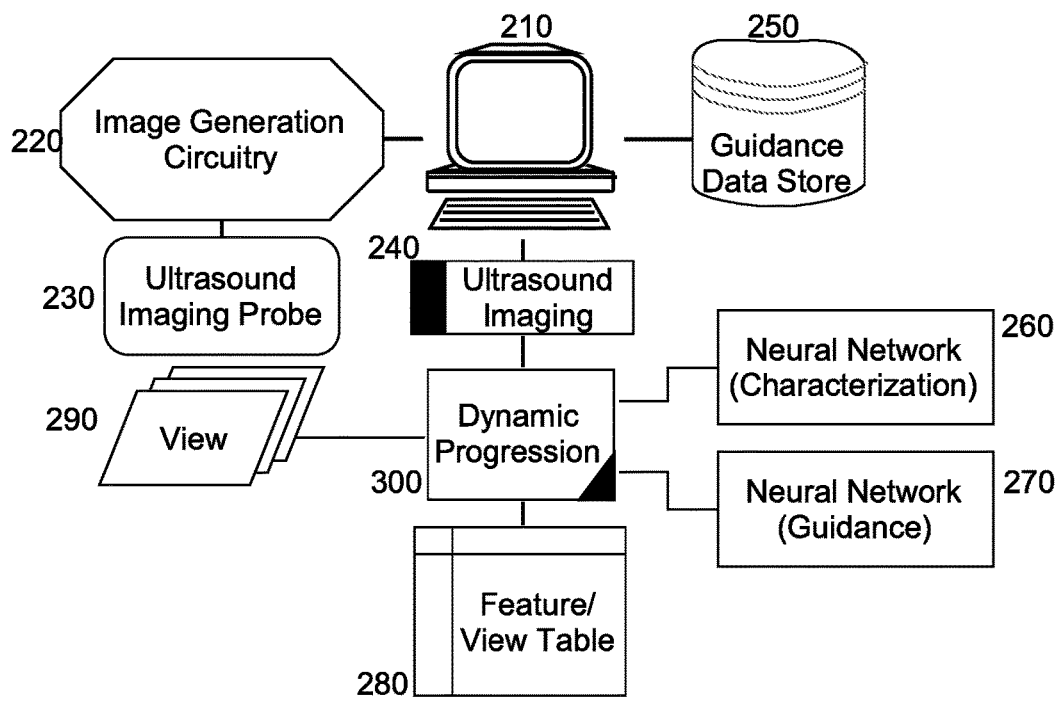
FIG. 2 is a schematic illustration of an ultrasound diagnostics data processing system configured for ultrasound guidance dynamic progression; and, FIG. 3 is a flow chart illustrating a process for ultrasound guidance dynamic progression.

The process described in connection with FIG. 1 can be implemented within an ultrasound diagnostics data processing system. In further illustration, FIG. 2 schematically shows an ultrasound diagnostics data processing system configured for ultrasound guidance dynamic progression. The system includes a host computing system 210 that includes a computer with at least one processor, memory and a display. The host computing system 210 also includes a data store 250. The host computing system 210 yet further is coupled to an ultrasound imaging system 240 adapted to generate ultrasound imagery acquired through the placement of an imaging wand 230 proximate to a target organ of interest in a mammalian subject by operation of image generation circuitry 220. The host computing system 210 is communicatively coupled to fixed storage (not shown), either locally or remotely ("in the cloud") storing therein one or more neural networks 260 and a programmatic interface to the neural networks 260.

The neural network 260 is trained to characterize one or more features of the target organ, for example an ejection fraction value of a heart, or the presence or absence of aortic stenosis, or the presence or absence of a structural feature of the target organ. To do so, generated imagery of a specified view of the target organ acquired by the ultrasound imaging system 240 is provided to the neural network 260 which in turn accesses the programmatic interface so that the neural network 260 may then output the characterization for the generated imagery along with an indication of confidence in that characterization. The ultrasound imaging system 240 in turn renders on the display of the host computing system 210 not only the generated imagery, but also the characterization and optionally, the indication of confidence in that characterization.

As well, a second neural network 270 may be trained to characterize guidance instructions relative to contemporaneously acquired imagery of the target organ. In this regard, with respect to a particular one of the views 290, the second neural network 270 is trained to produce recommend guidance to achieve the optimal acquisition of generated imagery for the target organ for the particular one of the views 290, relative to the generated imagery contemporaneously presented in a display of the host computing system 210. To that end, as the neural network 270 is presented with contemporaneously acquired imagery of the target organ for the particular one of the views 290, the neural network produces a recommended movement or pose of the ultrasound imaging probe 230 in order to acquire generated imagery deemed acceptable for the particular one of the views 290.

Importantly, a dynamic progression module 300 is coupled to the ultrasound imaging system 240. The dynamic progression module 300 includes computer program instructions that when executing in the memory of the host computing system 210, are enabled to group together a sequence of different views 290 as a workflow and, for each of the views 290 in the sequence, retrieve from the data store 250 guidance instructions necessary to optimally acquire generated imagery for the selected one of the views 290. The program instructions are further enabled to receive from the neural network 260 in characterizing acquired generated imagery for a selected one of the views 250 of a workflow, an indication of an anomalous feature, such as the presence of an unexpected structural feature, or the absence of an expected structural feature.

The program instructions of the module 300 then are adapted to correlate the anomalous feature with a particular one of the views 290 in a table 280, whether included as part of the contemporaneous workflow or otherwise. Finally, the program instructions of the module 300 are enabled to retrieve guidance from the data store 250 for the correlated one of the views 290 and to display the retrieved guidance in a display of the host computing system 210 in lieu of guidance for a next one of the views 290 in the contemporaneous workflow.

Figure 3:
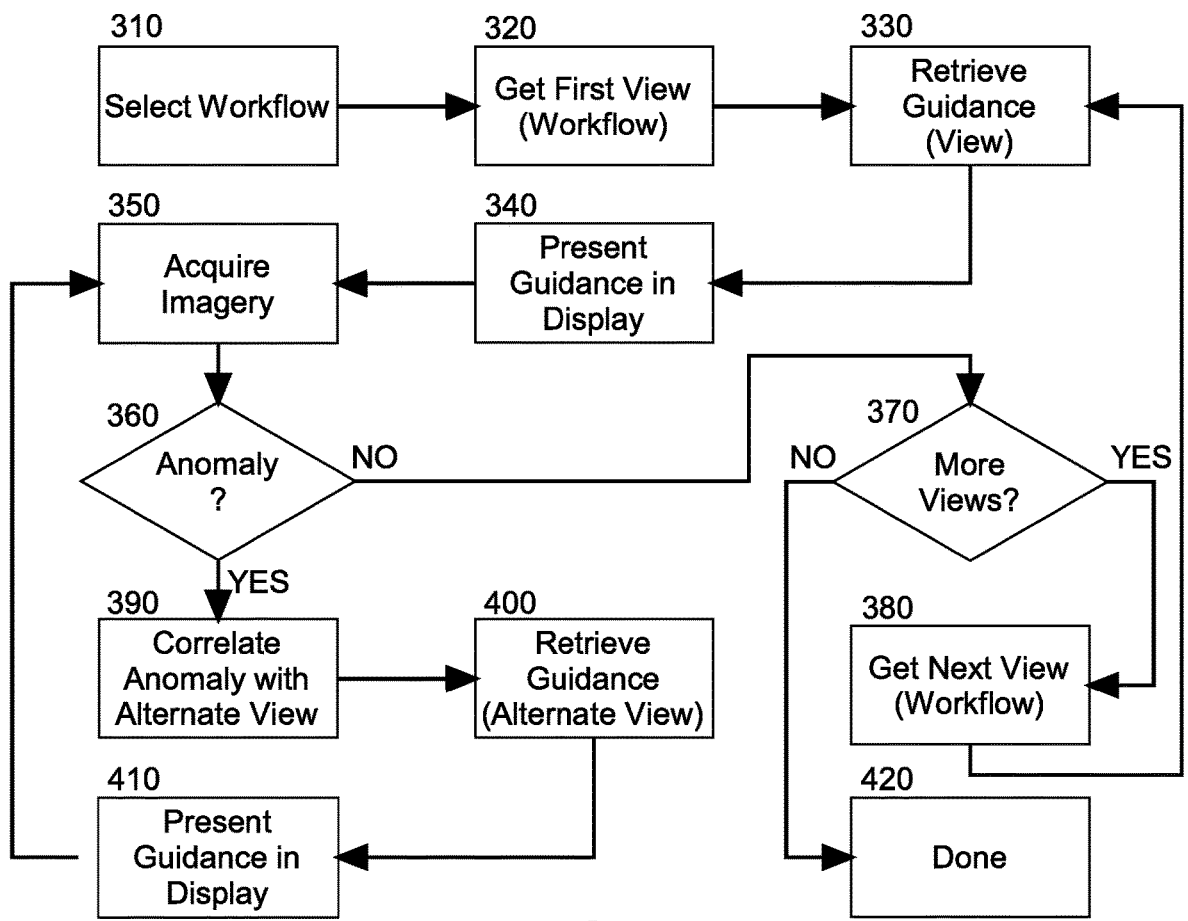

In even yet further illustration of the operation of the dynamic progression module 300, FIG. 3 is a flow chart illustrating a process for ultrasound guidance dynamic progression. Beginning in block 310, a workflow is selected including a multiplicity of different views of a target organ. In block 320, a first one of the views is selected for acquiring generated imagery of the target organ and in block 330, guidance instructions for the first view are retrieved into memory for display in a user interface to the ultrasound imaging system. In this regard, the guidance instructions may be retrieved from a fixed data store irrespective of any contemporaneous imagery acquired for the first view, or the guidance instructions may be selected based upon the output of a neural network trained to produce guidance instructions for a particular view based upon the content of contemporaneous imagery acquired for the first view. In either circumstance, in block 340, the guidance instructions are displayed in the user interface to the ultrasound imaging system.

In block 350, imagery is acquired in the ultrasound imaging system for the target organ. In decision block 360, it is determined whether or not an anomalous feature exists in connection with the acquired imagery. For instance, the imagery may be submitted to a neural network trained to classify anomalous features such as the presence or absence of structural elements of a target organ. If no anomalous features are determined to exist in the acquired imagery, in decision block 370 it is determined if additional views remain to be processed in the workflow. If so, a next view of the workflow is selected and the process repeats in block 330. Otherwise, the process proceeds to block 390.

In block 390, responsive to a determination that an anomalous feature has been detected in connection with the acquired imagery, the anomalous feature is correlated with an alternate view. In this regard, the anomalous feature of the target organ is a presence of a visible feature in the acquired imagery the absence of a visible feature in the acquired imagery, a visible feature correlated with a disease, an irregular characteristic of a structure of the target organ, or extraneous material on a structure of the target organ. As it will be understood, the anomalous feature may be correlated with a particular measurement helpful in better understanding the anomalous feature, such as the measurement of fluid flow in respect to a structure of the target organ. Such measurements may include, by way of example, the measurement of the velocity of blood flow through the structure of the target organ.

In block 400, guidance for the alternate view is retrieved. Finally, in block 410 the guidance for the alternate view is presented in the user interface for the ultrasound imaging system so as to provoke a dynamic change in the views of the workflow in response to having detected the anomalous feature of the acquired imagery. Thereafter, the process returns to decision block 350 in which new imagery is acquired and in decision block 360 it is determined if additional anomalous features are detected in the newly acquired imagery. Thereafter, in decision block 370, if it is determined that no additional views remain to be processed in the workflow, the process ends in block 420.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. An ultrasound guidance dynamic progression method comprising:
   selecting a predetermined ultrasound diagnostic workflow in a memory of an ultrasound diagnostic computing system, the workflow comprising a sequence of views to be imaged of a target area of target organ and anomalous features correlated with one or more of the views;
   selecting a first one of the views in the sequence and presenting guidance in a display of the computing system for the selected first one of the views;
   acquiring imagery in the computing system in association with the selected first one of the views in the sequence;
   detecting an anomalous feature of the target organ in the selected first view;
   determining that the anomalous feature of the target organ correlates with an alternative view, among the sequence of views, of the target organ that is different from the selected first view; and
   dynamically responding to the detection of the anomalous feature mid-procedure by presenting guidance instructions in the display for the correlated alternative view of the target organ that is different from the selected first view in lieu of guidance instructions for a next view of the sequence of views.

2. The method of claim 1, wherein the anomalous feature is correlated in the memory of the computing system with a disease.

3. The method of claim 1, wherein the anomalous feature is extraneous material on a structure of the target area of the target organ.

4. A data processing system configured for ultrasound guidance dynamic progression, the system comprising:
   a computer with memory and at least one processor;
   a display coupled to the computer;
   image generation circuitry coupled to the computer and the display;
   an ultrasound imaging probe comprising a transducer connected to the image generation circuitry; and
   an ultrasound guidance dynamic progression module executing in the memory of the computer, the module comprising program code enabled upon execution by the processor of the computer to perform:
      selecting a predetermined ultrasound diagnostic workflow in a memory of the computer, the workflow comprising a sequence of views to be imaged of a target area of target organ and anomalous features correlated to one or more of the views;
      selecting a first one of the views in the sequence and presenting guidance in a display of the computer for the selected first one of the views;
      acquiring imagery in the computer in association with the selected first one of the views in the sequence;
      detecting an anomalous feature of the target area of the organ in the selected first view;
      determining that the anomalous feature of the target organ correlates with an alternative view, among the sequence of views, of the target organ that is different from the selected first view; and
      dynamically responding to the detection of the anomalous feature mid-procedure by presenting guidance instructions in the display for the correlated alternate view of the target organ that is different from the selected first view in lieu of guidance instructions for a next view of the sequence of views.

5. The system of claim 4, wherein the anomalous feature is correlated in the memory of the computing system with a disease.

6. The system of claim 4, wherein the anomalous feature is extraneous material on a structure of the target area of the target organ.

7. A computer program product for ultrasound guidance dynamic progression, the computer program product including a non-transitory computer readable storage medium having program instructions embodied therewith, the program instructions executable by a device to cause the device to perform a method including:
  selecting a desired predetermined ultrasound diagnostic workflow in a memory of an ultrasound diagnostic computing system, the workflow comprising a sequence of views to be imaged of a target area of target organ and anomalous features correlated with one or more of the views;
  selecting a first one of the views in the sequence and presenting guidance in a display of the computing system for the selected first one of the views;
  acquiring imagery in the computing system in association with the selected first one of the views in the sequence;
  detecting an anomalous feature the target area of the organ in the selected first view;
  determining that the anomalous feature of the target organ correlates with an alternative view, among the sequence of views, of the target organ that is different from the selected first view; and
  dynamically responding to the detection of the anomalous feature mid-procedure by presenting guidance instructions in the display for the correlated alternate view of the target organ that is different from the selected first view in lieu of guidance instructions for a next view of the sequence of views.

8. The computer program product of claim 7, wherein the anomalous feature is correlated in memory of the computing system with a disease.

9. The computer program product of claim 7, wherein the anomalous feature is extraneous material on a structure of the target area of the target organ.

* * * * *